US 10,285,846 B2

(12) United States Patent
Lee

(10) Patent No.: US 10,285,846 B2
(45) Date of Patent: May 14, 2019

(54) CATHETER OF INFECTION PROTECTIVE STRUCTURE FOR INSERTION INTO URETHRA OF CHILD

(71) Applicant: Keun Ho Lee, Siheung-si (KR)

(72) Inventor: Keun Ho Lee, Siheung-si (KR)

( * ) Notice: Subject to any disclaimer, the term of this patent is extended or adjusted under 35 U.S.C. 154(b) by 394 days.

(21) Appl. No.: 14/896,355

(22) PCT Filed: May 29, 2014

(86) PCT No.: PCT/KR2014/004778
§ 371 (c)(1),
(2) Date: Dec. 4, 2015

(87) PCT Pub. No.: WO2014/196763
PCT Pub. Date: Dec. 11, 2014

(65) Prior Publication Data
US 2016/0120688 A1    May 5, 2016

(30) Foreign Application Priority Data
Jun. 5, 2013  (KR) .................. 10-2013-0064590

(51) Int. Cl.
*A61F 5/44* (2006.01)
*A61M 25/00* (2006.01)
(Continued)

(52) U.S. Cl.
CPC .......... *A61F 5/4405* (2013.01); *A61M 25/005* (2013.01); *A61M 25/0043* (2013.01);
(Continued)

(58) Field of Classification Search
CPC .......... A61F 5/4405; A61M 2025/0063; A61M 2210/1089; A61M 25/0043; A61M 2210/1092; A61M 2210/1096
See application file for complete search history.

(56) References Cited

U.S. PATENT DOCUMENTS 3,672,372 A * 6/1972 Heimlich .......... A61M 25/0017
604/247
3,867,945 A * 2/1975 Long .................. A61M 25/00
604/170.02
(Continued)

FOREIGN PATENT DOCUMENTS

JP         08299431 A      11/1996
JP     2011250903 A      12/2011
(Continued)

OTHER PUBLICATIONS

International Search Report of PCT/KR2014/004778 (dated Jul. 15, 2014).
PCT/IPEA of PCT/KR2014/004778 (Apr. 28, 2015).

*Primary Examiner* — Adam Marcetich

(57) ABSTRACT

Disclosed herein is a urethral catheter with an anti-infection structure for infants in which, in a state in which a hose is combined with a main pipe in advance, the reinforcement rod is inserted into/released from a urethral insertion pipe through a reinforcement rod inflow and outflow pipe separately formed at one side of the main pipe to prevent leakage of urine. When the reinforcement rod is inserted into the urethral insertion pipe in the combined state of the hose with the urethral insertion pipe and is then released from the urethral insertion pipe, setting of a urine storage bag is completed, thereby shortening a time to install of the urine storage bag, reducing medical staff's trouble, and preventing contamination and infection of a patient and the medical staff due to leakage of urine from the bag to the outside.

4 Claims, 5 Drawing Sheets

(51) Int. Cl.
  *A61M 25/01*   (2006.01)
  *A61M 25/09*   (2006.01)
  *A61M 25/10*   (2013.01)
  *A61B 17/34*   (2006.01)
  *A61M 27/00*   (2006.01)

(52) U.S. Cl.
  CPC ..... *A61M 25/1018* (2013.01); *A61B 17/3415* (2013.01); *A61M 25/0102* (2013.01); *A61M 27/00* (2013.01); *A61M 2025/0063* (2013.01); *A61M 2210/1089* (2013.01)

(56) References Cited

U.S. PATENT DOCUMENTS

| | | | | |
|---|---|---|---|---|
| 4,149,535 | A * | 4/1979 | Volder | A61M 5/1582 604/164.01 |
| 4,645,490 | A * | 2/1987 | Rosenberg | A61M 25/10 604/103 |
| 5,078,688 | A * | 1/1992 | Lobodzinski | A61M 25/0606 604/167.05 |
| 5,290,244 | A * | 3/1994 | Moonka | A61M 5/32 604/158 |
| 5,395,352 | A * | 3/1995 | Penny | A61M 25/1025 137/606 |
| 5,523,092 | A * | 6/1996 | Hanson | A61F 2/06 424/423 |
| 5,916,153 | A | 6/1999 | Rhea | |
| 6,001,078 | A * | 12/1999 | Reekers | A61M 25/0068 604/264 |
| 6,371,944 | B1 * | 4/2002 | Liu | A61M 25/06 604/284 |
| 2001/0005785 | A1 * | 6/2001 | Sachse | A61M 25/0054 604/530 |
| 2008/0086110 | A1 * | 4/2008 | Galdonik | A61M 25/00 604/509 |
| 2008/0114333 | A1 * | 5/2008 | Copa | A61M 25/0097 604/513 |
| 2011/0118704 | A1 * | 5/2011 | Riaz | A61M 25/04 604/544 |
| 2011/0218520 | A1 * | 9/2011 | Andrich | A61M 25/0017 604/544 |
| 2012/0095432 | A1 * | 4/2012 | Nath | A61B 17/3415 604/500 |
| 2012/0172822 | A1 * | 7/2012 | Gilman | A61F 5/4405 604/328 |
| 2012/0209203 | A1 * | 8/2012 | Gibertoni | A61B 17/3415 604/164.11 |
| 2013/0096428 | A1 * | 4/2013 | Gillies | A61M 25/065 600/434 |

FOREIGN PATENT DOCUMENTS

| | | |
|---|---|---|
| JP | 2013043010 A | 3/2013 |
| KR | 1020110087310 A | 8/2011 |

* cited by examiner

CATHETER OF INFECTION PROTECTIVE STRUCTURE FOR INSERTION INTO URETHRA OF CHILD

This application is a 371 of PCT/KR2014/004778 filed May 29, 2014, which claims the benefit of foreign priority of Korean Patent Application No. 10-2013-0064590 filed Jun. 5, 2013, the subject matter of which is hereby incorporated by reference in its entirety.

BACKGROUND OF THE INVENTION

Field of the Invention

The present invention relates to a urethral catheter with an anti-infection structure for infants which is used for infants having a narrower urethral canal than adults and, more particularly, to a urethral catheter with an anti-infection structure for infants in which, in order to prevent contamination generated when a hose is combined with a main pipe after insertion of the catheter into the urethra of patient, a reinforcement rod is inserted into and released from a reinforcement rod inflow and outflow pipe separately formed at a side of the main pipe under the condition that the hose is combined with the main pipe in advance so as to prevent urine from leaking during combination of the hose with the main pipe and to provide ease in insertion of the flexible urethral catheter for infants into the urethra.

Description of the Related Art

As is well known, catheters are flexible fine pipes which are inserted into veins, the urethra and the chest. Here, a urethral catheter is inserted into the urethra of a patient and executes a function of discharging patient's urine.

A conventional urethral catheter for infants 2, as exemplarily shown in FIG. 1, is inserted into the urethra of a patient with reduced mobility, guides and discharges patient's urine to an the urine storage bag 20, and includes a flexible fine pipe, i.e., a urethral insertion pipe 4 configured to be inserted into the urethra and a balloon 40 formed at a designated part of the front end of the urethral insertion pipe 4 to maintain a through hole 6 and the front end of the urethral insertion pipe 4 within the bladder so that urine may be introduced into the urethral insertion pipe 4.

A Y-shaped connection pipe 8 is provided at the lower end of the urethral insertion pipe 4 so as to communicate with the urethral insertion pipe 4. The Y-shaped connection pipe 8 includes a main pipe 10 and a branch pipe 16, the branch pipe 16 may be provided with a connection terminal 18 formed at the end thereof and combined with a water injector (or a balloon expander) to expand the balloon 40 formed at the front end of the urethral injection pipe 4, the main pipe 10 is provided with an insertion hole 12 with which a coupling front end 28 of a hose 22 connected to the urine storage bag 20 is coupled, and a projection 14 is formed on the inner circumferential surface of the insertion hole 12.

The urine storage bag 20 is a synthetic resin bag provided with an inlet and an outlet and serving to store urine discharged from the patient's urethra, and includes a discharge pipe 24 formed at the outlet, an opening/closing intermitting member 26 to intermit opening/closing of the hose 22 connected to the inlet, and a separate connector and a cap 30 combined with the coupling front end 28 of the hose 22 to prevent contamination.

Although the urethral insertion pipe 4 is inserted into the urethra of the patient, since the patient is an infant and has a narrow urethral canal, the urethral insertion pipe 4 needs to be flexible and causes a difficulty in insertion into the urethra of the patient. Therefore, in order to increase rigidity of the urethral insertion pipe 4 to easily insert the urethral insertion pipe 4 into the urethra of the patient, after the urethral insertion pipe 4 is inserted into the urethra of the patient under the condition that a reinforcement rod 32 is inserted into the urethral insertion pipe 4 through the insertion hole 12 of the main pipe 10, the reinforcement rod 32 is released from the urethral insertion pipe 4 and, then, the coupling front end 28 of the hose 22 is combined with the insertion hole 12 to communicate the urethral insertion pipe 4 with the urine storage bag 20.

However, in the conventional urethral catheter for infants 2, during a process of inserting the urethral insertion pipe 4 into the urethra of the patient, releasing the reinforcement rod 32 from the urethral insertion pipe 4 and then combining the coupling front end 28 of the hose 22 with the insertion hole 12, the patient may be exposed to the risk of contamination and infected with germs. Since the conventional urethral catheter for infants 2 requires the reinforcement rod 32, the separately provided hose should be combined with the catheter despite the rise of infection.

SUMMARY OF THE INVENTION

Therefore, the present invention has been made in view of the above problems, and it is an object of the present invention to provide a urethral catheter with an anti-infection structure for infants in which, in order to prevent contamination generated due to sameness between the inflow and outflow position of a reinforcement rod and the attachment position of a hose, the reinforcement rod is inserted into and released from a reinforcement rod inflow and outflow pipe separately formed at one side of a main pipe under the condition that the hose is combined integrally with the main pipe in advance, so as to prevent urine from leaking during combination of the hose with the main pipe and to prevent contamination and infection generated thereby as well as to provide ease in insertion of the flexible urethral catheter for infants into the urethra of an infant.

In accordance with the present invention, the above and other objects can be accomplished by the provision of a urethral catheter with an anti-infection structure for infants, including a urine storage bag configured to store urine, a hose being connected to one end of the urine storage bag, a urethral insertion pipe inserted into the urethra of a patient to guide and discharge urine to the urine storage bag, a reinforcement rod configured to allow the urethral insertion pipe to be easily inserted into the urethra of the patient, and a double Y-shaped connection pipe formed at the rear end of the urethral insertion pipe and including a main pipe connected to a hose, a branch pipe connected to a water injector or a balloon expander to expand a balloon provided at the front end of the urethral insertion pipe and a reinforcement rod inflow and outflow pipe to insert and release the reinforcement rod into and from the urethral insertion pipe, wherein the reinforcement rod is released from the urethral insertion pipe through the reinforcement rod inflow and outflow pipe under the condition that the hose is combined with the main pipe, so as to prevent leakage of urine when the hose is combined with the main pipe.

The hose may be combined integrally with the main pipe and the reinforcement rod may be released from the urethral insertion pipe through the reinforcement rod inflow and outflow pipe provided at one side of the main pipe.

The reinforcement rod inflow and outflow pipe may include a check valve provided therein to prevent leakage of urine through an inlet when the reinforcement rod is released from the urethral insertion pipe or execute the function of a check valve.

The urethral catheter for infants may further include a plug to prevent leakage of urine through the check valve or execution of the function of the check valve by the reinforcement rod inflow and outflow pipe.

The entirety or a part of the inlet of the reinforcement rod inflow and outflow pipe may be in the stenosed state at all times and thus, when the reinforcement rod is inserted into the urethral insertion pipe, the reinforcement rod may be inserted into the urethral insertion pipe while opening the inlet, and when the reinforcement rod is released from the urethral insertion pipe, the inlet may be closed so that urine does not open the inlet so as not to leak to the outside.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, preferred embodiments of the present invention will be described with reference to the annexed drawings.

Figure 1:
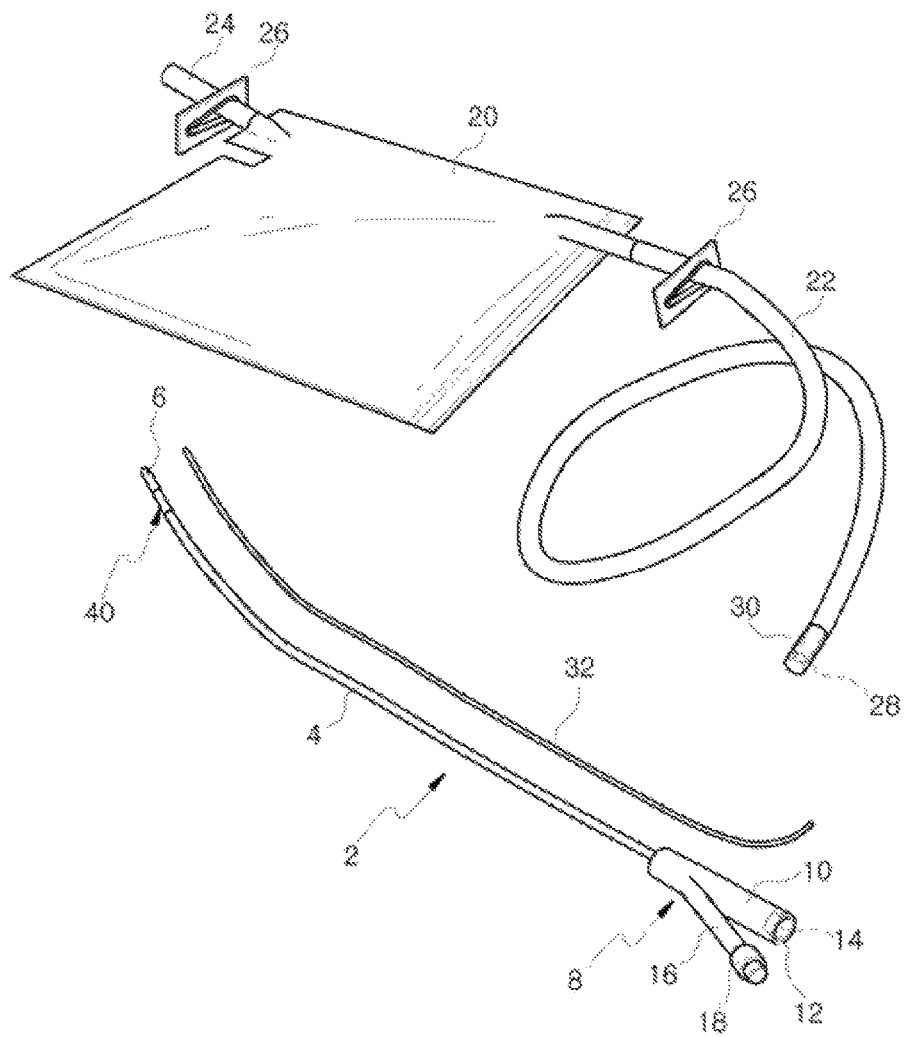
FIG. 1 is a perspective view illustrating a conventional urethral catheter.
Figure 2:
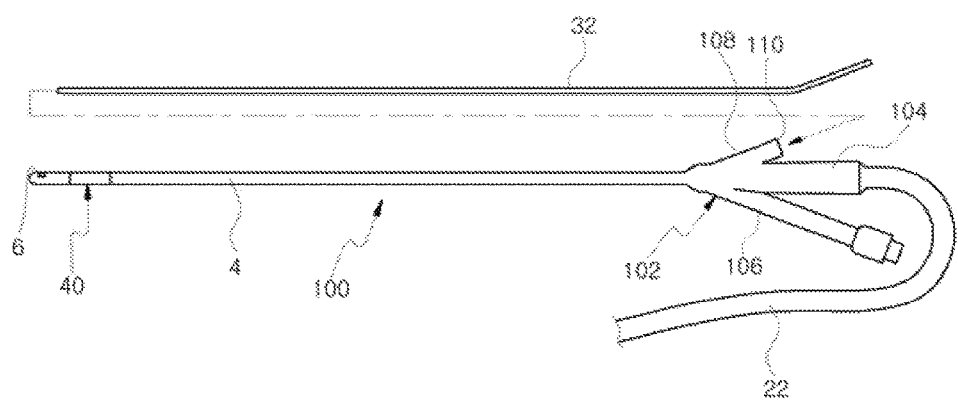
FIG. 2 is a perspective view illustrating a urethral catheter with an anti-infection structure for infants in accordance with one embodiment of the present invention.
Figure 3:
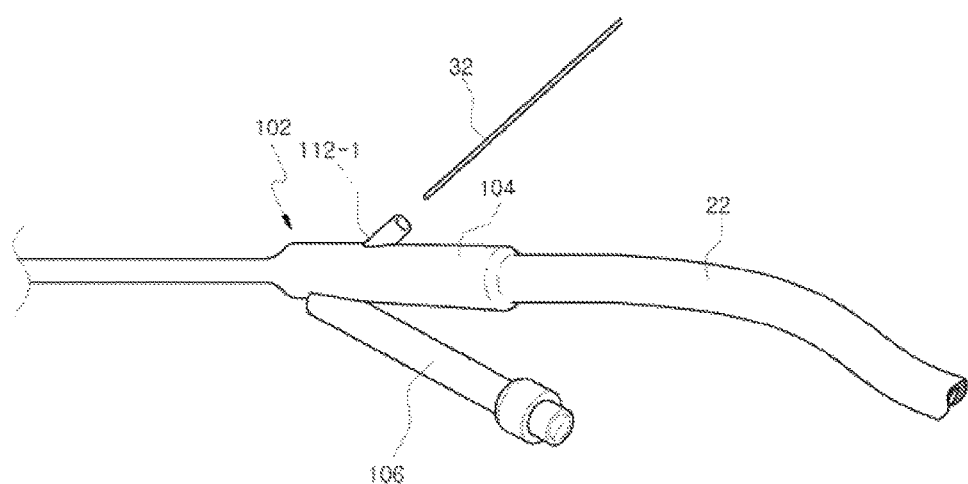
FIG. 3 is an enlarged perspective view of a double Y-shaped connection pipe of the urethral catheter for infants in accordance with the embodiment of the present invention.

FIG. 2 is a perspective view illustrating a urethral catheter with an anti-infection structure for infants in accordance with one embodiment of the present invention and FIG. 3 is an enlarged perspective view of a double Y-shaped connection pipe of the urethral catheter for infants in accordance with the embodiment of the present invention.

With reference to FIGS. 2 and 3, a urethral catheter with an anti-infection structure for infants 100 in accordance with one embodiment of the present invention is a urethral catheter in which, in order to prevent contamination generated due to sameness between the inflow and outflow position of a reinforcement rod and the attachment position of a hose, in a state in which a hose is combined integrally with a main pipe in advance, a urethral insertion pipe is inserted into the urethra of a patient under the condition that the reinforcement rod is inserted into the urethral insertion pipe through a reinforcement rod inflow and outflow pipe separately formed at one side of the main pipe and, then, the reinforcement rod is released from the urethral insertion pipe, thereby preventing leakage of urine during combination of the hose with the main pipe.

In more detail, the urethral catheter for infants 100 in accordance with the embodiment of the present invention includes a urethral insertion pipe 4 inserted into the urethra of a patient to guide urine so as to discharge the urine to a urine storage bag 20, and a double Y-shaped connection pipe 102 provided integrally with the rear end of the urethral insertion pipe 4.

A through hole 6, through which urine in the urethra may be introduced into the urethral insertion pipe 4, is formed at the front end of the urethral insertion pipe 4 and the double Y-shaped connection pipe 102 communicating with the inside of the urethral insertion pipe 4 is formed at the rear end of the urethral insertion pipe 4.

The double Y-shaped connection pipe 102 includes a main pipe 104 connected to a hose 22, a branch pipe 106 connected to a water injector (or a balloon expander) to expand a balloon 40 provided at the front end of the urethral insertion pipe 4, and a reinforcement rod inflow and outflow pipe 108 through which a reinforcement rod 32 is inserted into and released from the urethral insertion pipe 4.

Therefore, in a state in which the hose 22 is combined with the main pipe 104 in advance, the urethral insertion pipe 4 is supplied to medical staff under the condition that the reinforcement rod 32 is inserted into the urethral insertion pipe 4 through the reinforcement rod inflow and outflow pipe 108, and the medical staff insert the urethral insertion pipe 4 into the urethra of a patient, then release the reinforcement rod 32 from the urethral insertion pipe 4 through the reinforcement rod inflow and outflow pipe 108 and may thus prevent leakage of urine when the hose 22 is combined with the main pipe 104.

That is, in the urethral catheter for infants 100 in accordance with the embodiment of the present invention, the inflow and outflow position of the reinforcement rod 32 and the combination position of the hose 22 are different, the reinforcement rod 32 is inserted into the urethral insertion pipe 4 through the reinforcement rod inflow and outflow pipe 108 in the state that the hose 22 is combined with the main pipe 104 and, when the urethral insertion pipe 4 is inserted into the urethra of the patient and then the reinforcement rod 32 is released from the urethral insertion pipe 4, urine discharged through the urethral insertion pipe 4 passes through the hose 22 through the main pipe 104 and thus does not leak to the outside.

Further, the urethral catheter for infants 100 in accordance with the embodiment of the present invention is configured such that, when the reinforcement rod 32 is released from the urethral insertion pipe 4, urine discharged through the urethral insertion pipe 4 passes through the hose 22 via the main pipe 104 and does not leak to the outside through the reinforcement rod inflow and outflow pipe 108.

For this purpose, the reinforcement rod inflow and outflow pipe 108 may include a check valve 112-1 provided therein so as to allow the reinforcement rod 32 to be inserted into and released from the reinforcement rod inflow and outflow pipe 108 and to prevent urine from leaking to an inlet 110.

Here, the check valve 112-1 may be separately provided or the reinforcement rod inflow and outflow pipe 108 may execute the function of a check valve.

That is, the inlet 110 of the reinforcement rod inflow and outflow pipe 108 is in the stenosed state at all times and, thus the reinforcement rod 32 may be inserted into reinforcement rod inflow and outflow pipe 108 in the direction of the urethral insertion pipe 4 while opening the inlet 110 and urine discharged through the urethral insertion pipe 4 may not open the inlet 110 with its own pressure. Therefore, the reinforcement rod inflow and outflow pipe 108 may execute the function of a check valve to prevent leakage of urine.

Here, in order to completely block leakage of a small quantity of urine generated due to operation of the check valve 112-1 or operation of the reinforcement rod inflow and outflow pipe 108 executing the function of a check valve, a plug to close the inlet 110 after removal of the reinforcement rod 32 from the inlet 110 may be further provided.

Now, functions and effects of the urethral catheter for infants 100 in accordance with the embodiment of the present invention will be described in detail with reference to the accompanying drawings.

Figure 4:
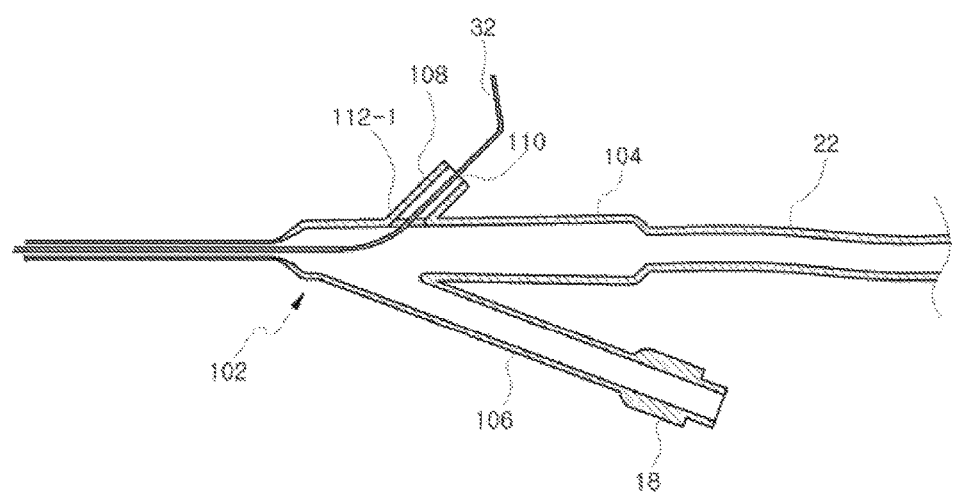
FIG. 4 is a cross-sectional view illustrating a state in which a reinforcement rod is inserted into the urethral catheter for infants in accordance with the embodiment of the present invention.
Figure 5:
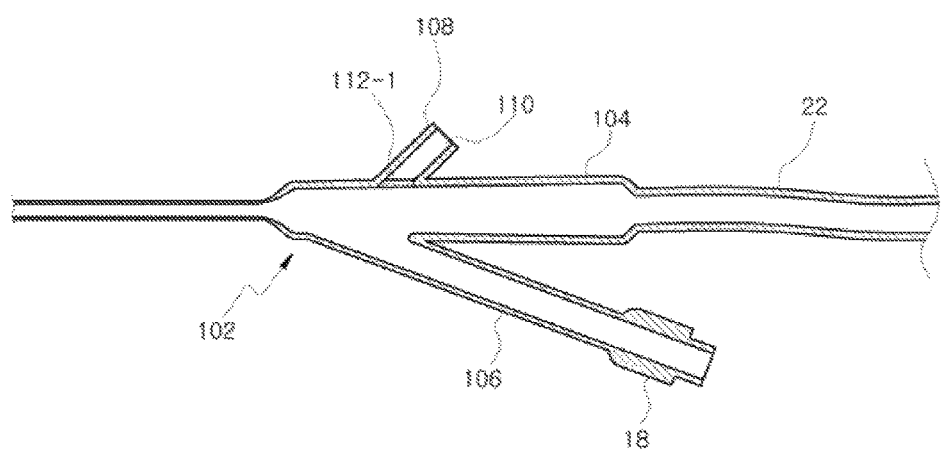
FIG. 5 is a cross-sectional view illustrating a state in which the reinforcement rod is released from the urethral catheter for infants in accordance with the embodiment of the present invention.

FIG. 4 is a cross-sectional view illustrating a state in which the reinforcement rod is inserted into the urethral catheter for infants in accordance with the embodiment of the present invention and FIG. 5 is a cross-sectional view illustrating a state in which the reinforcement rod is released from the urethral catheter for infants in accordance with the embodiment of the present invention.

First, in a state in which the urethral catheter for infants 100 in accordance with the embodiment of the present invention and the hose 22 provided with one end, with which the urine storage bag 20 is combined, are separated from each other, the hose 22 is combined with the main pipe 22 of the double Y-shaped connection pipe 102.

In such a state, the reinforcement rod 32 is inserted into the urethral insertion pipe 4 through the reinforcement inflow and outflow pipe 108 formed at a designated part of the double Y-shaped connection pipe 102.

Here, since the entirety or a part of the inlet 110 of the reinforcement rod inflow and outflow pipe 108 is in the stenosed state at all times, when the reinforcement rod 32 is inserted into the inlet 110 in the direction of the urethral insertion pipe 4, the reinforcement rod 32 may be inserted into the inlet 110 while opening the inlet 110.

The urethral catheter for infants 100 in such a state is supplied to medical staff, and the medical staff insert the urethral insertion pipe 4 into the urethra of a patient and inject water into the urethral insertion pipe 4 through the branch pipe connection terminal 18 and thus expand the balloon 40 so as to prevent the urethral insertion pipe 4 from being separated from the patient's body.

Since urine needs to be supplied along the inside of the urethral insertion pipe 4 in the state in which the urethral insertion pipe 4 is completely inserted into the urethra of the patient, the reinforcement rod 32 is released from the reinforcement rod inflow and outflow pipe 108 to the outside.

Then, since the inlet 110 of the reinforcement rod inflow and outflow pipe 108 maintains the stenosed state at all times, urine discharged through the urethral insertion pipe 4 passes through the hose 22 via the main pipe 104 and is collected in the urine storage bag 20 but, urine does not open the inlet 110 of the reinforcement rod inflow and outflow pipe 108 with its own pressure and thus the reinforcement rod inflow and outflow pipe 108 executes the function of a check valve.

In addition to the check valve 112-1 or execution of the function of a check valve by the reinforcement rod inflow and outflow pipe 108, the plug may be inserted into the inlet 110 so as to block leakage of a small quantity of urine generated through the check valve 112-1.

Therefore, in the urethral catheter for infants 100 in accordance with the embodiment of the present invention, the reinforcement rod 32 is released from the urethral insertion pipe 4 in the state in which the hose 22 is combined with the urethral insertion pipe 4 in advance and, thus, the urine storage bag 20 may be very rapidly set, as compared to a conventional urethral catheter in which a hose is combined with a urethral insertion pipe after release of a reinforcement rod from the urethral insertion pipe, thereby reducing medical staff's trouble. Further, the urethral catheter for infants 100 in accordance with the embodiment of the present invention may prevent contamination and infection of a patient and medical staff generated due to leakage of urine to the outside during a process of combining the hose 22 with the urethral insertion pipe 4.

As apparent from the above description, the present invention provides a urethral catheter with an anti-infection structure for infants in which a hose is combined with a urethral insertion pipe in advance, the urethral insertion pipe is supplied to medical staff under the condition that a reinforcement rod is inserted into the urethral insertion pipe through a reinforcement rod inflow and outflow pipe, and the medical staff insert the urethral insertion pipe into the urethra of a patient and then releases the reinforcement rod from the urethral insertion pipe to complete setting of a urine storage bag, thereby shortening a time taken to install of the urine storage bag and reducing medical staff's trouble. Further, the urethral catheter for infants in accordance with the present invention may prevent contamination and infection of the patient and the medical staff generated due to leakage of urine from the urine storage bag to the outside during such a process.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A pediatric urinary catheter device, comprising:
    a catheter having an elongated body, the catheter having an insertion pipe disposed on the distal portion of the catheter, the insertion pipe defining a urine drainage channel, the distal end of the insertion pipe having a closed end, the insertion pipe having a through hole formed on the side of the distal end of the insertion pipe, the catheter having a urine drainage port, a branch port, and a rod port disposed on the proximal portion of the catheter, and
    a reinforcement rod, the rod port configured to insert and release the reinforcement rod directly into and from the insertion pipe, the distal end of the reinforcement rod configured to be blocked by the closed distal end of the insertion pipe, the rod port having a check valve configured to be closed when the reinforcement rod is entirely released from the catheter such that the urine drainage channel is solely diverted to the urine drainage port.

2. The pediatric urinary catheter device according to claim 1, wherein a hose is combined integrally with the urine drainage port so as to prevent leakage of urine when the reinforcement rod is released from the insertion pipe.

3. The pediatric urinary catheter device according to claim 1, wherein the branch port is configured to connect to a balloon expander.

4. The pediatric urinary catheter device according to claim 1, wherein the rod port has a plug to prevent leakage of urine through the check valve.

* * * * *